United States Patent [19]

Tokinaga et al.

[11] Patent Number: 4,628,035

[45] Date of Patent: Dec. 9, 1986

[54] IMMUNOASSAY METHOD

[75] Inventors: Daizo Tokinaga; Teruaki Kobayashi, both of Hachioji; Kazumichi Imai, Kokubunji, all of Japan

[73] Assignee: Hitachi, Ltd., Tokyo, Japan

[21] Appl. No.: 638,423

[22] Filed: Aug. 7, 1984

[30] Foreign Application Priority Data

Sep. 9, 1983 [JP] Japan .............................. 58-164992

[51] Int. Cl.$^4$ .......................................... G01N 33/543
[52] U.S. Cl. ........................................ 436/518; 435/7; 435/8; 436/514; 436/515; 436/516; 436/528; 436/529; 436/530
[58] Field of Search ............... 435/7, 8; 436/514, 516, 436/530, 531, 518; 204/1 T, 403

[56] References Cited

U.S. PATENT DOCUMENTS 4,452,901 6/1984 Gordon et al. ................ 436/516 X

FOREIGN PATENT DOCUMENTS 2737491 2/1978 Fed. Rep. of Germany ...... 436/516

Primary Examiner—Christine M. Nucker
Assistant Examiner—Stephen C. Wieder
Attorney, Agent, or Firm—Antonelli, Terry & Wands

[57] ABSTRACT

An immunoassay method for measuring a concentration of an antigen for a short period of time by immobilizing an antibody over the whole zone of an effective supporting matrix for electrophoresis and fixing an antigen in a sample to be measured by electrophoresis for the antigen-antibody reaction between said immobilized antibody and said antigen.

19 Claims, 7 Drawing Figures

IMMUNOASSAY METHOD

BACKGROUND OF THE INVENTION

The present invention relates to an immunoassay technique and in particular relates to a novel immunoassay method for quantitatively measuring a concentration of an antigen or an antibody in a sample.

There was reported by Yalow et al. (Nature, 184; 1948) a technique of measuring a slight amount of insulin by use of a specific antibody labelled with radioisotope. Since then, the measuring technique called radioimmunoassay has been utilized for the quantitative measurement of various biological materials and drugs. However, a problem at issue is the requiring of particular attention in handling, because of using a radioisotope. Thus, there have been investigated various immunoassay techniques utilizing nonisotopic labels such as enzyme, enzyme substrate, fluorescent and chemiluminescent materials. Above all, a technique of utilizing enzyme or fluorescent material as a label has reached a practical level. However, these techniques and the radioimmunoassay are still difficult to be automated, because of the labor and the time required for the entire process.

As a simplified technique for the entire process, one example that may be mentioned is that disclosed in U.S. Pat. No. 3,852,157 but in this patent an analyte is limited to haptens having a low molecular weight. This example shows the simplification of process without requiring an operation of separating an antigen-antibody complex from free antigens or antibodies. On the other hand, it has also been attempted to simplify the separation operation. The operation is called a solid phase method in which an antibody or antigen is bonded in advance on an insoluble carrier and the antigen-antibody reaction is caused on the carrier. The free antigens or antibodies are readily separable from the bound materials by washing the carrier with water.

The immunoassay process can be simplified by employing the solid phase method but many unsatisfactory points still remain in the aspect of the automation of the entire process. It is essential to shorten the time required for the entire process for automating the immunoassay. The antigen-antibody reaction requires time most in the immunoassay process and it usually takes several hours to one day therefor. It is usual that the required time becomes longer with the reduction of a concentration of material to be subject to the immunoassay.

For shortening the reaction time, there has been proposed a method of filling a column with microcrystals or fine particles bonded with an antibody (or antigen) and forcibly passing an analyte therethrough (Japanese Patent Publication No. 127823/78). This example shows a method of forcibly feeding a fluid itself such as the analyte into a portion or layer of a carrier in which an antibody or the like was immobilized.

As a method of feeding not a fluid wholly but only a specific component contained therein (e.g. a substance to be detected or the like), there is a method of selectively feeding a specific component by electrophoresis. In an example thereof, a portion of a gel layer disposed on a supporting plate is replaced with an antibody- or antigen-immobilized gel or porous matrix layer, and the antigen or antibody which is a material to be detected is fed into said portion (U.S. Pat. No. 3,966,897). In this case, the direction of feeding the material to be detected is necessarily parallel to a supporting plate surface, i.e. an antibody-immobilized layer surface.

Another example of employing the electrophoresis is shown in Japanese Patent Publication No. 132946/80. In this example, a gel tube filled with polyacrylamide for disk electrophoresis is prepared, and an antibody solution or antigen solution is poured into one end of the gel tube followed by electrophoresis thereby to form a concentrated layer of the antibody or antigen, and then the antigen-antibody reaction takes place in said concentrated layer while the antigen solution or antibody solution is being electrophoreted. It has also been tried to promote the formation of the concentrated layer by inserting a protein-impermeable membrane, e.g. a dialysis membrane, into a portion of the gel. Therein, the antibody or antigen is not immobilized in the supporting matrix for electrophoresis and is present in a free state in the reaction layer. Furthermore, because of being present in the free state in the reaction layer, the reaction layer itself cannot be directly contacted with an electrolyte solution in an anode side or in a cathode side of the electrophoresis.

In any of the antigen-antibody reaction methods utilizing the above cited two electrophoresis methods, the supporting matrix for electrophoresis (i.e. a portion free from the antibody or antigen) other than the reaction portion or reaction layer should necessarily be prepared. Thus, it is necessary to feed the antigen or antibody to the reaction portion or reaction layer through the supporting matrix for electrophoresis and accordingly, the distance of electrophoresis becomes longer and the time required for electrophoresis becomes longer. Furthermore, for effecting the immunoassay by employing these methods, an inhibitor e.g. an excess labelled antibody which does not participate in the reaction) fed to the reaction portion or reaction layer should be removed from the reaction portion or reaction layer. For this removal in the electrophoresis method, the electrophoresis should be further continued and in this case, more time is required for moving the inhibitor through the supporting matrix for electrophoresis other than the reaction portion or reaction layer.

SUMMARY OF THE INVENTION

An object of the present invention is to provide an improved immunoassay technique. Another object of the present invention is to shorten the time required for antigen-antibody reaction in immunoassay. A further object of the present invention is to provide an immunoassay technique that is readily carried out automatically.

These and other objects are attained by an immunoassay technique for fixing an antigen in a sample to an immobilized antibody by the antigen-antibody reaction and measuring the concentration of the antigen, which is characterized by comprising (a) a step of immobilizing the antibody over the whole zone of an effective supporting matrix for electrophoresis, (b) a step of fixing the antigen in the sample to be measured with said immobilized antibody by the antigen-antibody reaction in the course of moving said antigen by electrophoresis, (c) a step of moving the labelled antibody toward said fixed antigen by electrophoresis for reaction or transferring the labelled antigen to an unreacted portion of said immobilized antibody by electrophoresis for reaction, and (d) a step of measuring said labelled antibody or labelled antigen.

DETAILED DESCRIPTION OF PREFERRED EMBODIMENTS

In the above-mentioned two electrophoresis methods, the antigen or antibody must be moved in the supporting matrix for electrophoresis until the same reaches the reaction portion or reaction layer and too much time is required and, furthermore, additional time is required for moving the same in the supporting matrix for electrophoresis even in the removal of an unreacted material from the vicinity of the reaction portion or the vicinity of the reaction layer. The removal of the unreacted portion may be omitted when the reaction portion is taken out after completion of the reaction and the subsequent operation is effected. However, although this procedure shortens the time, it causes another problem such as making the operation complicated to be unfit for automation.

In the present invention, the supporting matrix for electrophoresis is substantially constituted only with the reaction portion. That is, the supporting matrix for electrophoresis is the reaction portion to the substantially all the portion of which the antibody or antigen was immobilized therein and which contacts directly an electrolyte solution in an anode side and an electrolyte solution in a cathode side. In this case, it is desirable for the purpose of shortening the time that the reaction portion is made in the form of a membrane and the antigen or antibody which is a reactant is moved by electrophoresis in the direction vertical to said membrane surface.

The present invention is carried out under a pH condition the analyte is charged in a specific environment, and as the immunoassay technique, almost all techniques in which a solid phase reaction such as sandwich method and immunosorbent assay are utilizable.

The present invention is further explained in detail with reference to the following examples.

EXAMPLE 1

An anti-human IgG antibody-immobilized cellulose acetate membrane was prepared by immersing a cellulose acetate membrane (having a thickness of about 120 μm) for electrophoresis in an anti-human IgG antibody (rabbit) solution for about 1 hour and then immersing the resulting membrane in a 2.5% glutaraldehyde solution diluted with PBS (0.1M phosphate buffer solution containing 1/15M NaCl, pH=7.4) for 30 minutes, said series of operations being repeated three times, then immersing the resulting membrane in an anti-human IgG antibody solution for about 1 hour and washing the membrane sufficiently with PBS. A round membrane having a diameter of 8 mm was cut out from the resulting membrane and immunoassay was carried out according to the sandwich technique by use of said round membrane as a reaction membrane and human IgG as an analyte.

Figure 1:
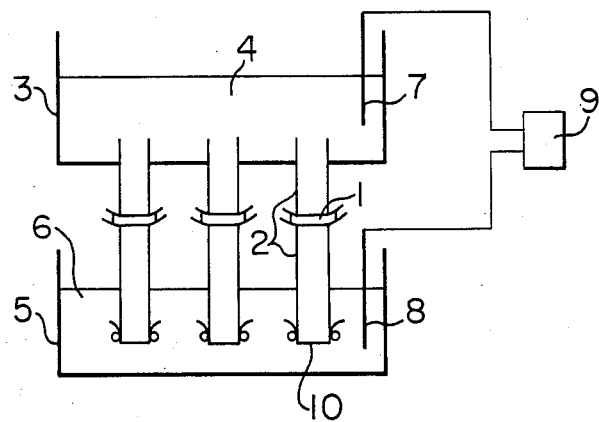
FIG. 1 is an schematic drawing showing an embodiment of an electrophoresis apparatus for effecting the antigen-antibody reaction.

The antigen-antibody reaction was carried out by use of an apparatus shown typically in FIG. 1. Reaction membrane 1 is held by glass-made ball joint 2 having an inner diameter of 4 mm. Upper electrolyte 4 and lower electrolyte 6, both comprising Tris-glycine buffer solution (pH=8.6), were put in upper electrolyte vessel 3 and lower electrolyte vessel 5, respectively. In addition, both 7 and 8 are platinum electrodes, 9 is DC source, and 10 is dialysis membrane.

Figure 2:
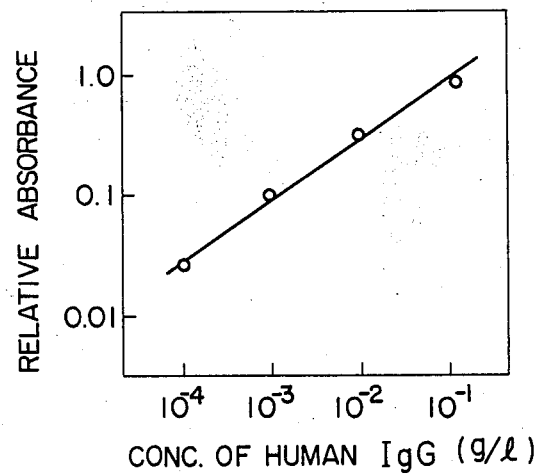
FIGS. 2, 3 and 4 are, respectively, drawings showing standard curves for human IgG, human albumin and human chorionic gonadotropin measured according to the present invention.

Firstly, 10 μl of a standard sample diluted with a 40% sucrose solution into double volume was gently poured into the upper part of the reaction membrane by use of a microsyringe. At the same time, three samples different from each other were poured onto three membranes. Then, the electrophoresis was done for 15 minutes at an applied voltage of 50 V. Next, 10 μl of commercial alkaline phosphatase-labelled anti-human IgG antibody (goat) solution (Miles Lab.) diluted with a 40% sucrose solution into double volume was poured onto the upper part of the reaction membrane and then the electrophoresis was effected for 15 minutes at an applied voltage of 50 V. Thenafter, the reaction membrane was taken out, and simply rinsed with PBS and the color development due to the enzyme activity of alkaline phosphatase present in the reaction membrane was made by immersing for 30 minutes into a liquid having a composition shown in Table 1. After the color development, the reaction membrane was washed with water, once dried and then immersed into decalin to transparentize the reaction membrane and the color development concentration was measured by colorimetry at a wavelength of 600 nm. The result is shown in FIG. 2. In addition, the ordinate in said figure shows a difference in absorbance between each color-developed sample and each color-developed sample obtained in the same operation as mentioned above except for a standard sample completely free from human IgG was poured.

TABLE 1

| | |
|---|---|
| Sodium naphthol AS-BI phosphate: | 10 mg |
| p-diazodimethylaniline chloride zinc chloride: | 30 mg |
| 10% magnesium chloride aqueous solution: | 2 drops |
| 0.1 M Tris-HCl buffer solution (pH = 8.6): | 50 ml |

EXAMPLE 2

An anti-human albumin antibody (rabbit)-immobilized polyacrylamide gel membrane (having a thickness of about 300 μm) was prepared as follows: That is, 25 μl of a 2.5% acrolein aqueous solution was added to 0.5 ml of a IgG fraction of an anti-human albumin anti serum (containing 2.4 mg/ml of an active antibody) and the resulting mixture was allowed to stand for 30 minutes under ice-cooling and then dialyzed with PBS. 1.5 ml of a 0.32 g/ml acrylamide solution, 1.5 ml of a 0.016 g/ml N,N'-methylene-bis-acrylamide solution, 1.25 ml of a 4.6 μl/ml N,N,N',N'-tetramethylene diamine aqueous solution, and 5.75 ml of a 1.2 mg/ml ammonium persulfate solution were added to the resulting mixture and the resultant mixture was well stirred and then, poured into a glass-made gel membrane-former and allowed to stand to gel, thereby preparing a membrane. A round membrane having a diameter of 9 mm was cut out from said membrane which was used as a reaction membrane similarly as in Example 1. In this case, however, in consideration of fragility of the antibody-immobilized polyacrylamide gel membrane, a polyester-made net having a thickness of 200 μm was inserted into the reaction membrane.

Figure 3:
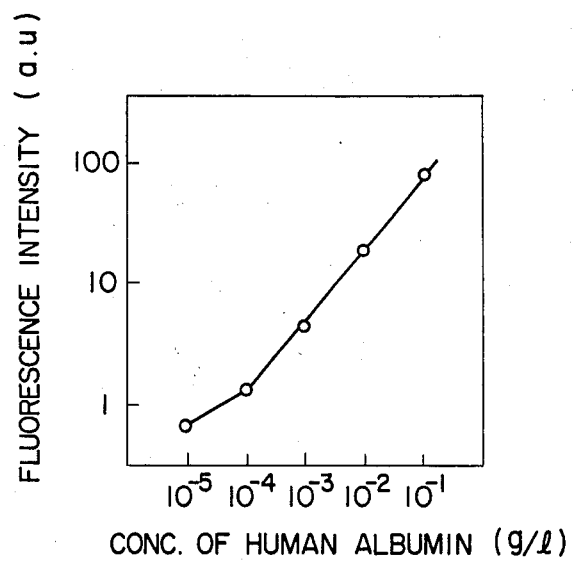

The sucrose-mixed liquid of the human albumin standard sample was poured onto the membrane similarly as in Example 1 and then, the electrophoresis was effected for 30 minutes at an applied voltage of 250 V and further, an anti-human albumin anti-serum (rabbit) labelled with fluoresein prepared according to M. Goldman's method was similarly poured thereonto and then, the electrophoresis was effected for 20 minutes at an applied voltage of 250 V. Then, the reaction membrane was taken out and simply rinsed with PBS and the fluorescence intensity of the membrane was measured by use of a fluorometer. In addition, the excitation wavelength was 485 nm and the measured wavelength was 520 nm. The result is shown in FIG. 3.

EXAMPLE 3

Figure 4:
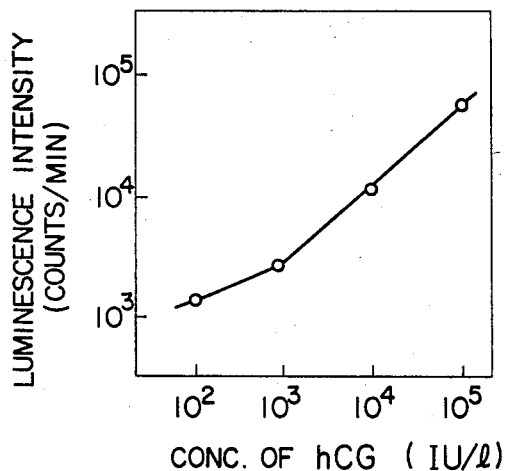

A polyacrylamide gel membrane (having a thickness of about 300 μm) immobilized with an IgG fraction obtained from an anti-human chorionic gonadotropin antiserum (rabbit) in the same manner as in Example 2 was prepared and used as a reaction membrane. The standard sample was set in the same manner as in Example 2 and then, a luminol-labelled antibody solution was similarly poured onto the membrane and electrophoreted for 30 minutes at 250 V. Then, the reaction membrane was taken out, immersed for 30 minutes in a 0.85% NaCl solution and then, placed at the bottom of an 1 cm square quartz cell with a transparent bottom window. 100 μl of a 0.1M $H_2O_2$ aqueous solution and 200 μl of a solution containing sodium hypochloride at a concentration of 10 mM in a 0.1N NaOH aqueous solution were added from the top to the cell thereby to cause oxidation luminescence of luminol in the reaction membrane and the luminescence amount was measured by a photon counter of which light-receiving part was disposed in the lower side of the quartz cell. The result was shown in FIG. 4.

EXAMPLE 4

Figure 5:
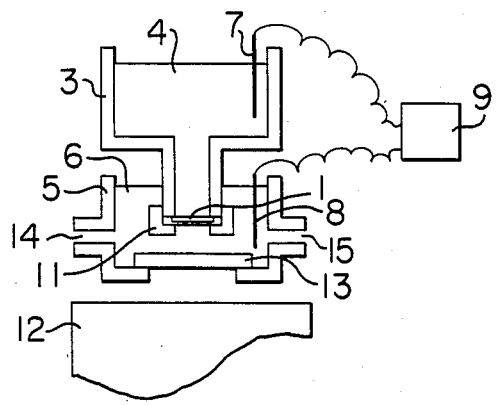
FIG. 5 is a drawing showing an example of a reaction membrane-holding system for carrying out the present invention.

The reaction membrane same as in Example 3 was placed in an acryl resin-made membrane holder shown in FIG. 5 and the standard sample and luminol-labelled antibody were moved similarly as in Example 3. In this Example, however, the electrolyte was continuously exchanged during the electrophoresis by gradually adding fresh electrolyte into the upper electrolyte vessel and unreacted material and the excess labelled antibody which were not reacted in the reaction membrane were removed. 14 is an inlet for the electrolyte and 15 is an outlet for the electrolyte. After the electrophoresis of the luminol-labelled antibody, the upper electrolyte in the upper electrolyte vessel and the membrane holder and the lower electrolyte in the lower electrolyte vessel were taken out and then, the $H_2O_2$ aqueous solution and the sodium hypochlorite solution were poured onto the membrane holder similarly as in Example 3 to cause luminescence of luminol and the luminescence amount was measured by a photon counter of which light-receiving part 12 was disposed in the lower side of the lower electrolyte vessel. In this case, there obtained also a good standard curve proportional to the added amounts of antigen, human chorionic gonadotropin, similarly as in Example 3.

EXAMPLE 5

Figure 6:
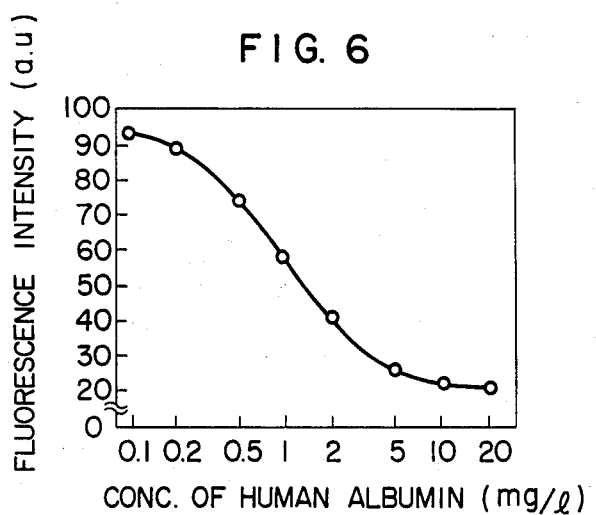
FIGS. 6 and 7 are drawings showing standard curves for human albumin measured according to the present invention.

The acrolein-anti-human albumin antibody conjugate solution prepared similarly as in Example 2 was diluted with PBS to 100-time volume and an antibody-immobilized polyacrylamide gel membrane was prepared by use of 0.5 ml of the resulting solution in the same manner as in Example 2. A round membrane having a diameter of 9 mm was cut out therefrom and used as a reaction membrane. The reaction membrane was placed in the same apparatus as in Example 2 and the human albumin standard sample was poured thereonto and the electrophoresis was performed for 45 minutes at an applied voltage of 100 V. Then, a fluorescein-labelled human albumin solution prepared according to M. Goldman's method was mixed in equal amount with a 40% sucrose solution and the resulting mixture was poured thereonto to perform the electrophoresis for 45 minutes at an applied voltage of 100 V. Thereafter, the reaction membrane was taken out therefrom and immersed for 5 minutes in PBS and then, the fluorescence intensity thereof was measured by fluorometer similarly as in Example 2. The result is shown in FIG. 6.

EXAMPLE 6

Gel membranes having different thicknesses were prepared by varying membrane-forming conditions of anti-human albumin antibody-immobilized polyacrylamide gel membranes. In addition, the composition at the time of gelling was same as in Example 2. The thicknesses of the obtained gel membranes were 20 to 200 μm. Each round membrane having a diameter of 9 mm was cut out from each gel membrane and set in an apparatus same as in Example 1. Then, 10 μl of the fluorescein-labelled anti-human albumin anti-serum solution mixed in equal amount with a 40% sucrose solution was poured thereonto and the electrophoresis was effected for 1 hour at an applied voltage of 250 V. The resulting membrane was taken out and rinsed with PBS for a short time and the amount of the fluorescein-labelled antibody remained in the membrane was measured by fluorometer. As a result, the remaining fluorescence was recognized on the membranes having a thickness over 1000 μm but the fluorescence producing matter was well removed from the membranes in the membranes in the membranes having a thickness of 1000 μm or less. Furthermore, the membranes having a thickness below 100 μm were fragile and very difficult to handle. From said matter, it was understood that the thickness of the anibody-immobilized polyacrylamide gel membrane was desirable to be in the range of 100 to 1000 μm.

EXAMPLE 7

By use of the reaction membrane, apparatus, reagent and measuring procedure same as in Example 2 and changing only the applied voltage at the time of the electrophoresis in the range of 20 to 1500 V, a suitable applied voltage was looked for. As a result, when the applied voltage went over 1000 V, the measured intensity of fluorescence was low and good calibration curve was not obtained. On the other hand, at an applied voltage lower than 50 V, good calibration curve was also not obtained because the remaining amount of fluorescence producing matter was much and background level was high. In a range of 50 to 1000 V, good calibration curves were obtained wherein the fluorescence intensity was proportional to the concentration of the added human albumin.

EXAMPLE 8

By use, as a reaction membrane, of an anti-human albumin antibody-immobilized polyacrylamide gel membrane prepared in the same manner as in Example 5, the immunoassay of the human albumin was effected according to competitive method.

Figure 7:
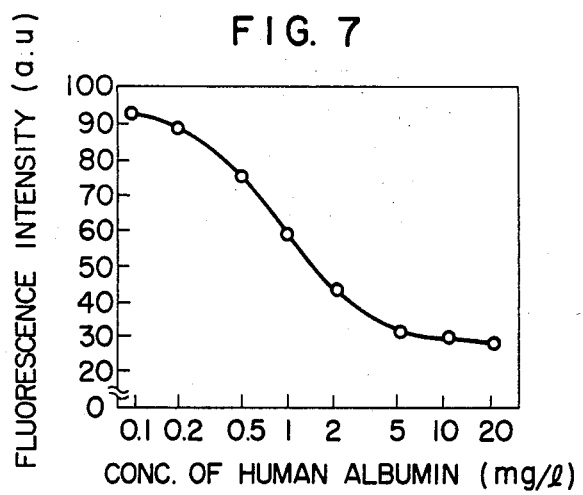

A sample prepared by adding a fluorescein-labelled albumin in an equal amount to the human albumin standard sample was electrophoreted for 45 minutes at an applied voltage of 100 V in the same manner as in Example 5. The labelling of fluorescein was effected according to the M. Goldman's method. After the electrophoresis, the reaction membrane was taken out and simply rinsed with PBS and the fluorescence intensity of the membrane was measured by fluorometer. In addition, the measuring conditions were same as in Example 2. The result is shown in FIG. 7.

As explained above, according to the present invention, the reaction time, costing 3 or 4 hours up to one day, required in one antigen-antibody reaction in the conventional immunoassay technique can be shortened within one hour. It is natural in the present invention that the required reaction time varies depending upon the kind of reaction membrane, the thickness of the reaction membrane, the hydrogen ion concentration and ionic strength of electrolytes at the time of electrophoresis, the applied voltage and the like. For example, the thickness of the antibody-immobilized polyacrylamine gel membrane used in Example 2 is about 300 μm but when the same is made thinner, the required reaction time can be further shortened at the same applied voltage.

As another effect of the present invention, it is pointed out that the process regarded as necessary in the conventional immunoassay can be simplified. That is, according to the present invention, the unreacted material and the excess labelled antibody move into the lower electrolyte vessel through the reaction membrane and hence, the operation such as washing with water which is regarded as necessary in the immunoassay based on the prior solid state reaction becomes unnecessary.

The above stated two effects in the present invention suggest that a whole automation apparatus of immunoassay is readily manufacturable. Because, the time required in immunoassay and the complication in process which are generally regarded as problems in the automatic immunoassay were simultaneously solved by the present invention.

As a further effect of the present invention, it is pointed out that the required amount of the labelled antigen is 10 μl or less according to the present invention and hence, the analytical cost can be reduced.

We claim:

1. An immunoassay method for measuring a concentration of an antigen contained in a sample by fixing said antigen with an immobilized antibody according to antigen-antibody reaction, comprising (a) a step of immobilizing an antibody over substantially the whole surface of a supporting matrix for electrophoresis; (b) a step of moving the antigen in the sample to be measured by electrophoresis with direct current to fix the antigen by the antigen-antibody reaction onto the immobilized antibody; (c) a step of moving a labelled antibody to said fixed antigen by direct current electrophoresis for reaction with said antigen; and (d) a step of measuring an enzyme activity, luminescence, or fluorescence of said labelled antibody to measure the concentration of the antigen in the sample.

2. An immunoassay method according to claim 1, wherein the antibody-immobilized matrix is a membrane.

3. An immunoassay method according to claim 2, wherein the membrane of the antibody-immobilized matrix is a porous cellulose acetate membrane.

4. A immunoassay method according to claim 2, wherein the membrane of the antibody-immobilized matrix ia a polyacrylamide gel membrane.

5. An immunoassay method according to claim 2, wherein a potential gradient is applied in a vertical direction to the surface of the antibody-immobilized matrix membrane and the antigen and the labelled antibody are subject to the electrophoresis in the vertical direction.

6. An immunoassay method according to claim 1, wherein the electrolyte in the electrophoresis direction is continuously exchanged in the step of (b) and (c).

7. An immunoassay method according to claim 4 wherein the antibody-immobilized polyacrylamide gel membrane is obtained by polymerization-crosslinking acrolein bonded in advance with the antibody with an acrylamide monomer and a N,N'-methylene-bis-acrylamine monomer.

8. An immunoassay method according to claim 1 wherein a labelling material for the labelled antibody is selected from the group consisting of enzymes, fluorescents and luminol.

9. An imunoassay method according to claim 4 wherein the thickness of the antibody-immobilized polyacrylamide gel membrane is within the range of 100 to 1000 μm.

10. An immunoassay method according to claim 5 wherein the applied voltage at the time of electrophoresis of the antigen and labelled antibody is within the range of 50 to 1000 V.

11. An immunoassay method for measuring a concentration of an antigen contained in a sample by fixing the antigen with an immobilized antibody according to antigen-antibody reaction, comprising (a) a step of immobilizing an antibody over substantially the whole surface of a supporting matrix for electrophoresis; (b) a step of moving the antigen in the sample to be measured by electrophoresis with direct current to fix the antigen by the antigen-antibody reaction onto the immobilized antibody; (c) a step of moving a labelled antigen to an unreacted portion of said immobilized antibody by direct current electrophoresis for reaction with said antibody; and (d) a step of measuring an enzyme activity, luminescence or fluorescence of said labelled antigen to measure the concentration of the antigen in the sample.

12. An immunoassay method according to claim 11, wherein the antibody-immobilized matrix is a membrane.

13. An immunoassay method according to claim 12, wherein the membrane of the antibody-immobilized matrix is a porous cellulose acetate membrane.

14. An immunoassay method according to claim 12, wherein the membrane of the antibody-immobilized matrix is a polyacrylamide gel membrane.

15. An immunoassay method according to claim 12, wherein a potential gradient is applied in a vertical direction to the surface of the antibody-immobilized matrix membrane, and the antigen, and the labelled antigen are subject to the electrophoresis in the vertical direction.

16. An immunoassay method according to claim 11, wherein the electrolyte in the electrophoresis direction is continuously exchanged in the steps of (b) and (c).

17. An immunoassay method according to claim 1, wherein a labelling material for the labelled antigen is selected from the group consisting of enzymes, flurescents and luminol.

18. An immunoassay method according to claim 14, wherein the thickness of the antibody-immobilized polyarcrylamide gel membrane is within the range of 100 to 1000 μm.

19. An immunoassay method according to claim 15, wherein the applied voltage at the time of electrophoresis of the antigen and labelled antigen is within the range of 50 to 1000 V.

* * * * *